United States Patent
Nanke et al.

(10) Patent No.: US 9,833,204 B2
(45) Date of Patent: Dec. 5, 2017

(54) COMPRESSION UNIT FOR X-RAY AND ULTRASOUND DIAGNOSITICS

(71) Applicant: SIEMENS AKTIENGESELLSCHAFT, Munich (DE)

(72) Inventors: Ralf Nanke, Neunkirchen am Brand (DE); Marcus Radicke, Furth (DE); Robert Standar, Pretzfeld (DE); Ulf Zimmermann, Aurachtal (DE)

(73) Assignee: Siemens Aktiengesellschaft, Munich (DE)

( * ) Notice: Subject to any disclaimer, the term of this patent is extended or adjusted under 35 U.S.C. 154(b) by 333 days.

(21) Appl. No.: 14/412,772

(22) PCT Filed: Jul. 5, 2013

(86) PCT No.: PCT/EP2013/064237
§ 371 (c)(1),
(2) Date: Jul. 24, 2015

(87) PCT Pub. No.: WO2014/009267
PCT Pub. Date: Jan. 16, 2014

(65) Prior Publication Data
US 2015/0351706 A1 Dec. 10, 2015

(30) Foreign Application Priority Data
Jul. 11, 2012 (DE) ........................ 10 2012 212 135

(51) Int. Cl.
*A61B 8/14* (2006.01)
*A61B 6/04* (2006.01)
(Continued)

(52) U.S. Cl.
CPC .......... *A61B 6/0414* (2013.01); *A61B 6/4417* (2013.01); *A61B 6/502* (2013.01);
(Continued)

(58) Field of Classification Search
CPC ..... A61B 6/032; A61B 6/0414; A61B 6/4417; A61B 6/502; A61B 8/0825; A61B 8/403; A61B 8/4281
See application file for complete search history.

(56) References Cited

U.S. PATENT DOCUMENTS

| 6,574,499 | B1 | 6/2003 | Dines et al. |
| 2003/0167004 | A1 | 9/2003 | Dines et al. |

(Continued)

FOREIGN PATENT DOCUMENTS

| DE | 102011083633 A1 | 3/2013 |
| WO | WO-2006/030406 A2 | 3/2006 |

OTHER PUBLICATIONS

Sinha et al. Automated Ultrasound Scanning on a Dual-Modality Breast Imaging System, Coverage and Motion Issues and Solutions, Journal of Ultrasound Medicine, vol. 26 (2007) pp. 645-655.

*Primary Examiner* — Mark Remaly
(74) *Attorney, Agent, or Firm* — Schiff Hardin LLP

(57) ABSTRACT

In a compression unit of a mammography apparatus, a breast is compressed between a first compression plane and a second compression plane. At least one of the first and second compression planes is formed by a fabric. The compression unit allows a breast to be maintained in a fixed, compressed state while acquiring an x-ray image of the compressed breast and the compressed state is maintained for subsequently acquiring an ultrasound image of the compressed breast.

10 Claims, 2 Drawing Sheets

(51) Int. Cl.
  *A61B 8/00* (2006.01)
  *A61B 6/00* (2006.01)
  *A61B 8/08* (2006.01)
  *A61B 6/03* (2006.01)

(52) U.S. Cl.
  CPC ............ *A61B 8/0825* (2013.01); *A61B 8/403* (2013.01); *A61B 8/4281* (2013.01); *A61B 6/032* (2013.01)

(56) References Cited

U.S. PATENT DOCUMENTS

| | | |
|---|---|---|
| 2006/0126794 A1 | 6/2006 | Hermann et al. |
| 2007/0280412 A1 | 12/2007 | Defreitas et al. |
| 2007/0282221 A1 | 12/2007 | Wang et al. |
| 2008/0103387 A1* | 5/2008 | Gross ............... A61B 6/0414 600/424 |
| 2009/0254006 A1* | 10/2009 | Babaev ............ A61B 17/00491 601/2 |
| 2010/0191104 A1 | 7/2010 | Suri et al. |
| 2012/0089026 A1* | 4/2012 | Wang ................ A61B 8/0825 600/443 |
| 2012/0238859 A1 | 9/2012 | Tokita et al. |

* cited by examiner

COMPRESSION UNIT FOR X-RAY AND ULTRASOUND DIAGNOSITICS

BACKGROUND OF THE INVENTION

Field of the Invention

The invention concerns a compression unit for a mammography apparatus.

Description of the Prior Art

Imaging methods are used for an effective diagnosis. In an imaging method, 2D x-ray images of a breast are acquired from different acquisition angles, for example during a circular arc-shaped trajectory around the subject, and calculated into a 3D data set. Starting from this 3D data set, slice exposures or x-ray images with an arbitrary slice approach through the 3D data set are created for a diagnosis and are relayed to a monitor in order to be assessed by a physician.

In order to be able to better assess a tissue variation for a diagnosis, additional ultrasound images of the breast tissue should be acquired. With sonography, echo pules can be received via the ultrasound pulses emitted by the ultrasound head, and these can be translated into an ultrasound image.

While the patient stands or sits in front of the mammography apparatus for an x-ray mammography examination, for an ultrasound examination the patient lies on a patient bed.

The x-ray images created with x-ray technology and the ultrasound images created with ultrasound technology can be rendered on a monitor next to one another or individually. For the assessment of the image content it is disadvantageous that the x-ray images and ultrasound images are created with different resolutions and the image content is shown from different viewing directions. An additional disadvantage is in that a repositioning of the patient must take place between the acquisition of the x-ray images and the ultrasound images, and the breast must be compressed with different strengths.

SUMMARY OF THE INVENTION

An object of the invention is to provide a compression unit for a mammography apparatus such wherein the disadvantages described above are overcome.

The above object is achieved in accordance with the present invention by a compression unit having a first compression unit component that forms a first compression plane, and a second compression unit component that forms a second compression plane, and a mechanism for adjusting a spacing between the first and second compression planes to compress a breast therebetween, and wherein at least one of said first compression plane and said second compression plane is formed from a fabric.

The invention has the advantage that the patient must be positioned only once for an ultrasound examination and x-ray examination.

The invention has the advantage that the ultrasound unit can be integrated in a space-saving manner into an existing compression unit of a mammography system.

The invention has the advantage that a spatial association can be established between distinctive areas in the x-ray image and ultrasound image.

The invention has the advantage that the specificity in a breast cancer diagnosis is significantly increased.

The invention has the advantage that the x-ray images and ultrasound images are subject to the same acquisition geometry.

The invention has the advantage that an image superposition of x-ray image and ultrasound image is possible.

The invention has the advantage that the extraction of a biopsy can take place immediately after an ultrasound acquisition and/or x-ray acquisition while maintaining the breast compression or fixing of the breast.

DESCRIPTION OF THE PREFERRED EMBODIMENTS

A compression unit of a mammography apparatus is described with which fixing of a subject for an x-ray exposure can be maintained up to the termination of an ultrasound acquisition.

Figure 1:
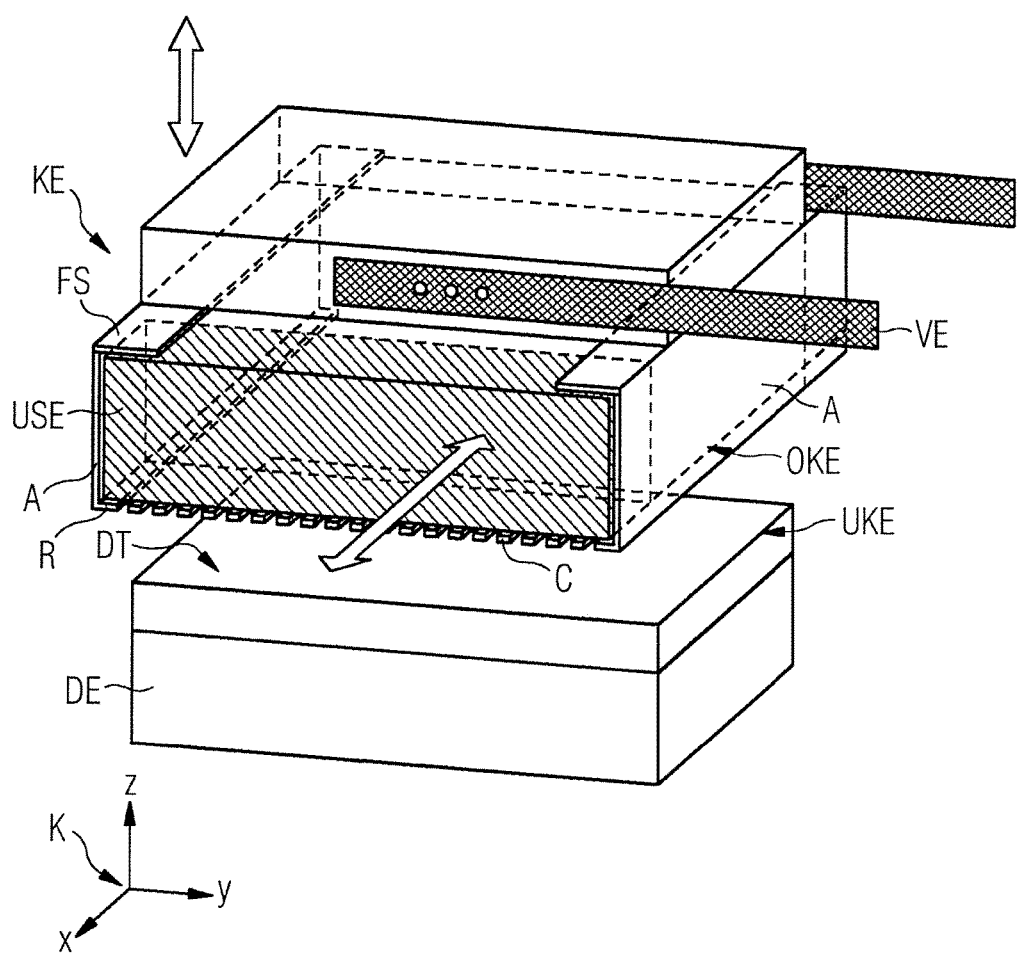
FIG. 1 is a perspective view of a compression unit in accordance with the present invention.

FIG. 1 shows a perspective presentation of a compression unit KE of a mammography apparatus MG. In this embodiment, the compression unit KE, is formed from a compression element C tensioned in a frame R. The compression unit KE shown in FIG. 1 has an ultrasound unit USE movable by a guide unit FS. The edge regions of the ultrasound unit USE are connected with elements of the guide unit FS so that said ultrasound unit USE or individual elements of the ultrasound USE can be vertically and/or horizontally displaced. The guide unit FS can be connected with a mount A. The mount A is connected via connection elements VE with a component support S, shown in FIG. 3 (for example the stand or the C-arm) of the mammography apparatus. During the x-ray image creation, the ultrasound unit USE is positioned outside of the acquisition region of the detector DE in a park position or rest position. The ultrasound unit USE can be moved corresponding to the arrangement and design of the guide elements FS in the x, y or z direction according to the imaged coordinate system K. The ultrasound unit USE can likewise be of matrix-like design, and the individual elements of the matrix can be controllable. The ultrasound unit USE can be composed of a number of individual elements, wherein the individual elements can additionally be moved—matched to one another—in the z-direction, in addition to an x-, y-movement. The feed can take place manually, manually/electromotorized, or exclusively supported by an electromotorized drive. In the shown embodiment, the ultrasound unit USE that is designed in a rod shape or matrix shape extends in the x-, y-direction.

Given a matrix-shaped embodiment of the ultrasound unit USE, during an ultrasound acquisition the coordinates of the individual ultrasound bodies are relayed to a superordinate computer to create a complete ultrasound image.

The compression unit KE has a first compression plane and second compression plane. The first compression plane OKE (which can also be designated as an upper compression plane) is formed by the compression element C and the second compression plane UKE (which can also be designated as a lower compression plane) can be formed by a placement surface. The placement surface can be formed either by the surface of the detector DE (which is movable in the x-, y-, z-directions) or by a separate placement plate DT movable in the x-, y-, z-directions. The first compression plane can be displaced to accordingly match the x-, y-, z-displacement of the second compression plane. The compression element C is formed by an element that is aligned to be planar. This compression element having planar alignment can be aligned parallel or at a slight angle to the lower compression plane. The compression element C is additionally designed such that this is permeable to x-rays and to ultrasound. For better coupling of the ultrasound waves with the examination subject, an ultrasound coupling gel is applied to the compression element C (by a dispenser unit that is not shown here) either before an x-ray acquisition or before the ultrasound examination. In an additional embodiment, a fluid gel adhering to the fabric can be applied to both sides of the compression element C (which is fashioned like fabric) before an ultrasound scanning. Instead of the application of the fluid gel, the compression element C (which can be stretched flat) can extend entirely or partially over the first compression plane. For example, the compression element C is tensioned in a rectangular frame R provided with tensioning elements. A flat planarity of the compression element C can be maintained in spite of a contact pressure on the compression element C that is generated by a breast M to be compressed. Depending on the composition and introduction of the compression element C, a convex or concave or curved surface can also result given a contact pressure on the compression element C.

The placement plate DT can also be designed corresponding to the compression element C. The ultrasound unit USE is then arranged below the compression element C. The ultrasound unit USE can likewise be formed from a plurality of individually addressable ultrasound elements. The movement of the ultrasound unit USE takes place as described in the x-, y-directions and as needed in the z-direction.

To introduce the fluid coupling gel, channel openings can be arranged at the edges of the ultrasound unit USE to apply the coupling gel to the compression element C.

Because the breast is compressed and fixed via the compression unit KE, first images B1 of the breast M are acquired with an x-ray source RQ and the detector unit DE. Second images B2 of the breast M are acquired with the ultrasound unit USE while maintaining the compression and fixing of the breast M.

The associated method enables an acquisition of first and second images B1, B2, wherein first images B1 of a subject M fixed in the compression unit KE are x-ray images acquired with an x-ray detector unit RQ, DE; and second images B2 (i.e. ultrasound images) of the fixed subject M are acquired by the ultrasound unit USE integrated into the compression unit KE. The compression of the subject M is maintained during and between the first images B1 and the second images B2. The compression of the subject M can also be maintained at a tissue extraction since the compression element C can be penetrated with a biopsy needle.

Figure 2:
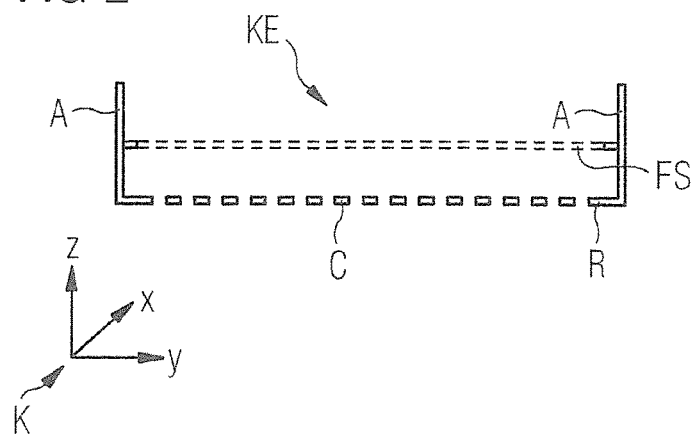
FIG. 2 is a side view of a portion of the compression unit shown in FIG. 1.

A side view of the upper part of the compression unit KE is shown in FIG. 2. In this embodiment, the compression element C is arranged on the lower edge of a mount A. This compression element C—for example a fabric or, respectively, a gauze—can be tensioned directly on the mount A or in a frame R. Given use of a frame R, this can be attached (to the mount A, for example) so as to be exchangeable and be integrated into the first compression plane OKE. The frame R and/or the mount A have tensioning elements to tension the fabric. The fabric in the mount A or the frame R can be tensioned by means of these tensioning elements. A flat or curved planarity of the fabric can arise given a contact pressure on the breast tissue to be compressed. Given the application of a fluid coupling gel, the fabric is fashioned in terms of its density and weave such that a coupling gel that is applied for ultrasound examination can be distributed in two dimensions between ultrasound head and examination subject. In a further embodiment, a two-dimensionally adhering coupling gel can be applied on the top side and underside of the compression element C. The consistency of the coupling gel is such that an ultrasound head in contact with this can be moved or driven thereon.

Figure 3:
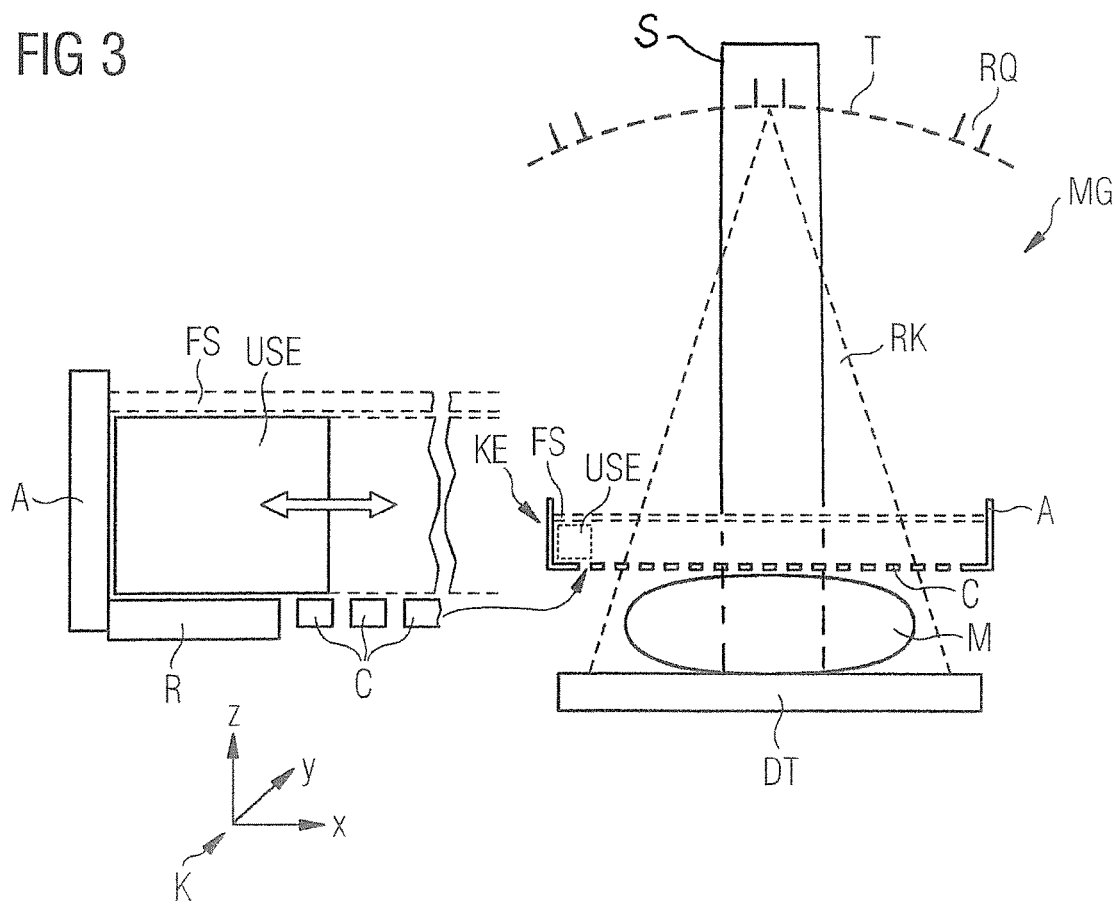
FIG. 3 is a front view of the compression unit shown in FIG. 1, with additional items being shown for explaining the operation of the compression unit.

A front view of the compression unit KE with a possible trajectory T of the x-ray source RQ of the mammography apparatus MG is shown in FIG. 3. In this schematically illustrated embodiment, the guide unit FS is arranged on the inside of the mount A of the compression unit KE, which mount A extends in the x-, y-directions. In the guide unit FS, the guide elements extending in the x-, y-direction are arranged for the feed of the ultrasound unit USE. In this shown embodiment, the ultrasound unit USE moves from left to right, as viewed from the patient. In the embodiment shown in FIG. 2, the ultrasound unit USE moves from or to a patient standing in front of the mammography apparatus, for example. The compression element C is arranged on the underside of the mount A. As was described above, the lower placement surface is fashioned with a compression element C. In this embodiment, an ultrasound unit USE to acquire ultrasound images is then arranged so as to be movable below the compression element C of the lower compression plane UKE.

The compression element C can be fashioned in the form of a web-like article, for example a gauze. The compression element C is permeable to both x-ray radiation and the ultrasound pulses emitted by the ultrasound unit USE and received. The compression of the breast can also be maintained during the ultrasound examination via the embodiment of the compression element C. The ultrasound unit USE can be positioned arbitrarily with regard to a horizontal displacement and a possible vertical displacement by the guide elements of the guide unit FS. During an x-ray acquisition or during a cycle of x-ray acquisitions, the breast remains fixed by the compression element C. The compression element C formed with the gauze is fashioned such that it maintains its flat planarity given a pressure on the compression element C. The coupling gel can be dispensed by the device between ultrasound unit USE and gauze, onto the already fixed breast M. A direct dispensing of the coupling gel before an ultrasound acquisition can take place over a large area, from multiple nozzles. These nozzles, connected with a storage container, can be attached to both sides of the ultrasound unit USE, and the gel stored in the storage container can be dispensed before a scanning process depending on the movement direction of the ultrasound unit USE. The ultrasound coupling gel can additionally be applied directly onto the subject, or onto the underside of the separating element, before a fixing of the breast. Instead of the fluid coupling gel, the compression element C can be coated with the gel layer both on its top side and underside. The coupling gel has the advantage that a direct transition of the ultrasound pulses into the breast tissue is enabled. The gauze provided with the coupling gel, tensioned in the frame, is arranged in the mount A so as to be exchangeable. The frame size of the frame R is variably selectable depending on its purpose. The individual 2D x-ray images acquired with the detector unit DE are calculated into a 3D data set in a computer (not depicted here) by a reconstruction algorithm. 2D x-ray images can be superimposed with 3D ultrasound images, and 3D x-ray images can be superimposed with a 3D ultrasound image or a 2D ultrasound image.

In addition to the advantage that the x-ray images and ultrasound images are present in a combinable presentation nearly in real time, the device has the advantage that the locality of a tissue variation can be determined and a biopsy can be extracted from this tissue at a precise point. For this purpose, a biopsy needle can be directly inserted into breast tissue with electronic control. During the biopsy extraction, the compression and fixing of the breast can also be maintained since the biopsy needle is insertable into the breast tissue either from the side or directly through the compression element C to extract the breast tissue.

An ultrasound exposure of the breast of a patient can also be acquired independently of an x-ray exposure. In this mode, the fixing process takes place by lowering the upper compression plane OKE and/or by raising the lower compression plane UKE. Because the breast is compressed and fixed, the ultrasound unit USE is drawn or directed along the surface of the breast M via guide elements of the guide unit FS.

For additional x-ray acquisitions—in particular for a tomosynthesis—the compression element C could be fashioned via selection of a determinable fabric design or, respectively, fabric composition, for example a partially different web density and/or a partially different elasticity. A convex shape of the compression element C can additionally be formed by a controllable tensioning device, for example a targeted loosening of the fabric. In this embodiment, the ultrasound unit USE is directed along the convex shape of the surface of the compression element or elements C.

The frame in which the compression element C is tensioned can extend over the entire breast or, over partial regions thereof.

Although modifications and changes may be suggested by those skilled in the art, it is the intention of the inventors to embody within the patent warranted heron all changes and modifications as reasonably and properly come within the scope of their contribution to the art.

The invention claimed is:

1. A mammography compression apparatus comprising:
    an upper compression assembly comprising a mount comprising parallel, spaced-apart guide elements with a fabric stretched across the guide elements to form a first compression plane, said fabric being permeable to x-rays and to ultrasound;
    a lower compression assembly comprising an x-ray radiation detector having a surface that forms a second compression plane, said first and second compression planes being adapted to receive a breast therebetween;
    a mammography apparatus support component to which said upper and lower compression assemblies are attached so that at least said upper compression assembly is movable, relative to said lower compression assembly, in a direction perpendicular to said first and second compression planes in order to compress the breast between the fabric and the surface of the x-ray radiation detector;
    an ultrasound applicator situated in a space in said upper compression assembly between said guide elements and adjacent to said fabric, said ultrasound applicator being guided and confined in said upper compression assembly by said guide elements so as to be movable on said fabric in at least one direction parallel to said first compression plane, while the breast is compressed by said fabric.

2. A compression unit as claimed in claim 1 wherein said fabric is attached to said guide elements so as to be selectively tensionable.

3. A compression unit as claimed in claim 1 comprising an ultrasound coupling gel on at least one side of said fabric.

4. A compression unit as claimed in claim 1 wherein said fabric is a gauze.

5. A mammography apparatus comprising:
    a component support;
    an x-ray source attached to said component support, said x-ray source emitting x-ray radiation;
    an upper compression assembly component comprising a mount comprising parallel, space-apart guide elements with a fabric stretched across the guide elements to form a first compression plane, said fabric being permeable to said x-ray radiation and to ultrasound;
    a lower compression assembly comprising a radiation detector that detects said x-ray radiation, said radiation detector having a surface that forms a second compression plane, said first and second compression planes being adapted to receive a breast therebetween;
    said upper and lower compression assemblies being attached to said component support so that at least said upper compression assembly is movable, relative to said lower compression assembly, in a direction perpendicular to said first and second compression planes in order to compress the breast between the fabric and the surface of the radiation detector;
    an ultrasound applicator situated in a space in said upper compression assembly between said guide elements and adjacent to said fabric, and being guided and confined in said upper compression assembly by said guide elements so as to be movable on said fabric in at least one direction parallel to said first compression plane while the breast is compressed by the fabric; and
    said upper and lower compression assemblies compressing the breast therebetween in a single position in order to sequentially irradiate the compressed breast in said single position with said x-ray radiation from said x-ray source and with ultrasound from said ultrasound applicator.

6. A mammography apparatus as claimed in claim 5 wherein said fabric is attached to said guide elements so as to be selectively tensionable.

7. A mammography apparatus as claimed in claim 5 comprising an ultrasound coupling gel on at least one side of said fabric.

8. A mammography apparatus as claimed in claim 5 wherein said fabric is a gauze.

9. A mammography apparatus as claimed in claim 5 wherein said component support is a vertical stand.

10. A mammography apparatus as claimed in claim 5 wherein said component support is a C-arm.

* * * * *